United States Patent [19]
Von Soiron

[11] 3,958,575
[45] May 25, 1976

[54] CONSTRICTING DEVICE FOR INCREASING PRESSURE ON HUMAN AND ANIMAL BODIES

[75] Inventor: Ferdinand Freiherr Von Soiron, Cologne, Germany

[73] Assignee: Prameta Prazisionsmetall-und Kunststofferzeugnisse G. Baumann & Co., Cologne, Germany

[22] Filed: Aug. 20, 1974

[21] Appl. No.: 498,963

[30] Foreign Application Priority Data
Aug. 23, 1973 Germany............................ 2342490

[52] U.S. Cl. .............................................. 128/327
[51] Int. Cl.² ........................................ A61B 17/12
[58] Field of Search ..................................... 128/327

[56] References Cited
UNITED STATES PATENTS
1,532,299 4/1925 Braecklein........................... 128/327
2,882,903 4/1959 Ramien............................... 128/327
FOREIGN PATENTS OR APPLICATIONS
457,314 11/1936 United Kingdom................. 128/327

*Primary Examiner*—Channing L. Pace
*Attorney, Agent, or Firm*—Diller, Brown, Ramik & Wight

[57] ABSTRACT

This disclosure relates to a constricting device for increasing pressure in humans and animals which includes an elongated member of flexible material looped upon itself to disposed ends thereof adjacent each other after passage through a fastener housing having clamping means therein, and the housing having an opening of a size to preclude the simultaneous passage therethrough of the ends. Preferably a first of the ends is received in a socket of a size and configuration to freely pass through the opening while a second end is received in another socket having a tongue projecting in a direction toward the housing and away from the end to which it is attached to preclude the latter from being drawn through the housing upon the removal of the device from use.

4 Claims, 4 Drawing Figures

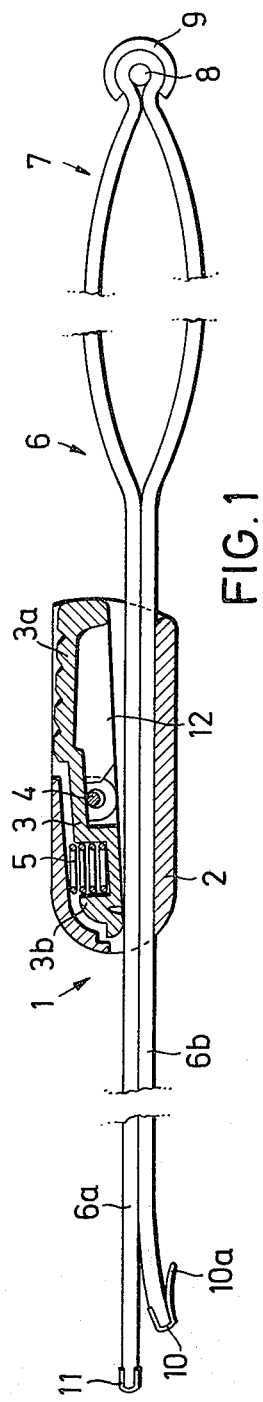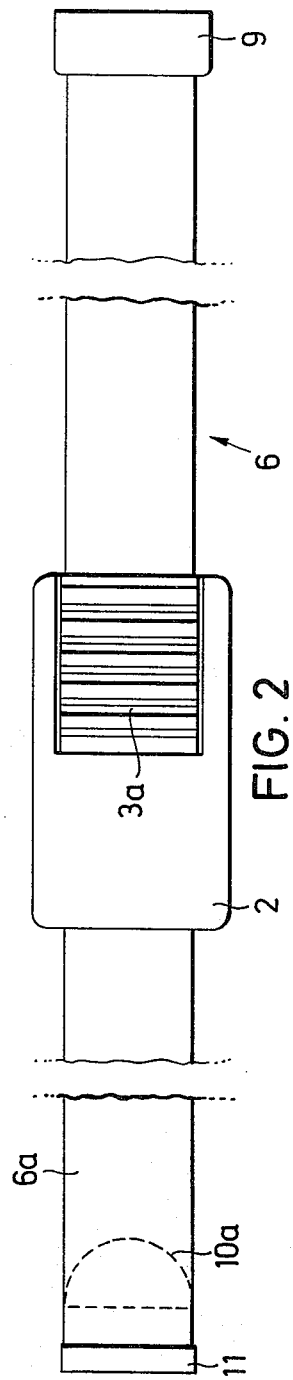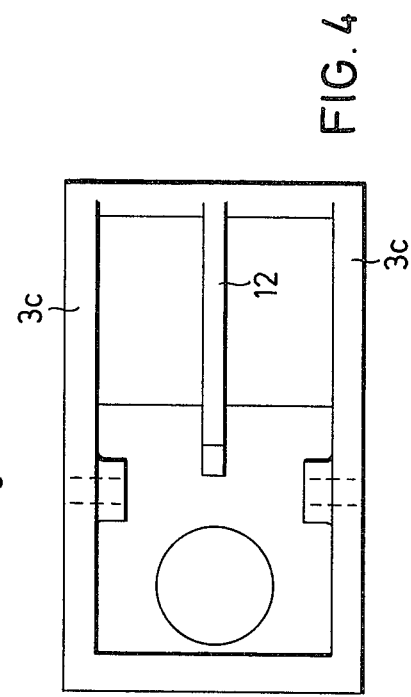

CONSTRICTING DEVICE FOR INCREASING PRESSURE ON HUMAN AND ANIMAL BODIES

The present invention relates to a constricting device for producing an increase in pressure in humans or animals as, for example is typically employed when drawing blood by the use of a hypodermic syringe, when taking blood pressure, or the like.

It is conventional to provide such constricting devices in the form of a cord or tape having a loop which is guided through a fastener housing carrying a pivotally mounted clamping lever. The fastener housing can be split along the length of the looped tape so that the loop can be set to any size desired. In order to prevent the fastener housing from being slide beyond the terminal ends of the tape or elongated member the ends of the tape are appropriately provided with enlarged end pieces or other means which preclude the bind passage thereof through an appropriate aperature of the fastener housing. Such devices include clamping sleeves which are pressmounted on the ends of the tape which is generally formed of rubber, and owing to their size they provide reliability against withdrawal of the tape through the opening or openings of the fastener housing.

When constricting devices of the type described are used there are cases in which it is desirable, for example, when working with a hypodermic syringe that the constricting device be released and removed from the particular body part involved because it presents an obstruction when simply loosened, instead of totally removed. In conventional mechanisms of this type it is necessary for the loop to be opened as far as possible and removed in a telescopic manner over the inserted hypodermic syringe which is not only an awkard operation but gives rise to the risk of the inserted hypodermic syringe being unintentionally touched, moved, pivoted, or other wise jarred, and effect which obviously can have highly undesired consequences.

In cases where the particular human or animal body parts are large it is possible that the tape loop cannot be opened sufficiently to enable it to be telescopically withdrawn together with the fastening housing over the hypodermic syringe and analogous accouterments. If the tape or elongated member is of a length which is sufficient for the last-mentioned case to be withdrawn by forming a highly enlarged loop such would be impractical for average applications because of the length of the fre ends thereof which would interfer with various operations and though are basically regarded as being superfluous under normal situations.

In view of the foregoing, it is a primary object of this invention to provide a constricting device of the type described which enables all activities to be performed in a simple and reliable manner with the tape being of a normal length thus avoiding the previously mentioned disadvantages. In accordance with this invention the constricting device is characterized by one free end of the tape having a socket or end part which is flat to permit the tape end to be drawn through the fastener casing and is advantageously attached to that portion of the loop which is longer than the remaining portion. With this construction it is possible to detach and remove the constricting device without the telescopic motion heretofore noted thereby by-passing any problems that might be encountered relative to an inserted or injected hypodermic syringe. By applying appropriate pressure on a clamping lever of the fastener or fastener housing the latter can be adjusted along the tape until the loop has been widened to the maximum possible extent and any further sliding motion of the fastener enables the tape with the smooth end piece to be pulled through the housing while the other end which has means for locking against the housing cannot be withdrawn therethrough. By this construction it is no longer necessary to withdraw the loop in a conventional telescopic manner while at the same time assuring that but a single portion of the tape is withdrawn from the fastener housing. This is particularly advantageous for large body parts, and obviously the length of the tape or elongated member need but be of the largest possible diameter without an increase being necessary for removal in a conventional manner thus avoiding conventionally suspended tape ends of known similar devices.

In further accordance with this invention the fastener housing and its associated clamping lever are constructed of plastic material and the latter includes a rib which forms a guide or sliding surface which greatly facilitates the withdrawal of the one tape end for the purposes of releasing the tape loop.

With the above and other objects in view that will hereinafter appear, the nature of the invention will be more clearly understood by reference to the following detailed description, the appended claimed subject matter, and the several views illustrated in the accompanying drawing.

IN THE DRAWING

FIG. 1 is a side elevational view through the constricting device of this invention with the fastener housing shown in cross section, and illustrates the manner in which the tape is looped and passed through the fastener housing with one end thereof being readily removed through the housing and the other end being provided with a depending tongue for contact against the housing to preclude the removal thereof therethrough.

FIG. 2 is a fragmentary top plan view of the constricting device of FIG. 1, and more clearly illustrates details thereof including a depressible clamping lever of the fastener housing and the curved configuration of the tongue carried by an end of the elongated member of tape.

FIG. 3 is an enlarged longitudinal sectional view taken through the clamping lever of FIG. 1, and illustrates in particular a downwardly directed rib position along a longitudinal center line of the clamping lever to assist in the guiding and sliding removal of one end of the tape through the housing.

FIG. 4 is a bottom view looking from bottom to top in FIG. 4 of the clamping lever, and more particularly illustrates details of the guide rib and trunnions for pivotally mounting the clamping lever to the fastener housing.

Referring to the drawing, a novel constricting device constructed in accordance with this invention for applying pressure particularly to human, but also to animal, body parts is generally designated by the reference numeral 1 and includes a fastener housing 2 in which is pivotally clamping mounted a clamping 3 by suitable journals 4. The clamping lever includes one end 3a which in effect is a depressible portion or push button and an opposite end which is the clamping end 3b bias normally to a clamping position by a spring 5 housed within a circular recess (unnumbered) of the clamping lever, best shown in FIGS. 1 and 4, and an underside (unnumbered) of the fastener housing 2. A resilient, flexible, elastic or like elongated member or tape 6 which is formed into a loop 7 by being guided about a pin 8 and fastened thereto by a clamp or sleeve 9 is passed through openings (unnumbered) of the housing 2 and has opposite terminal or free ends 6a, 6b.

In order to release the loop 7 from the appendage or like of a person or animal the fastener housing is slid toward the end 6a, 6b by depressing the depressible end portion 3a of the lever 3 and upon the release of clamping pressure at the clamping end 3b the housing 2 is slid until it contacts the tongue 10a. Further application of pressure on the fastener casing 2 in the direction toward the tape ends 11,10 causes the two tape parts 6a, 6b to be stressed or stretched as a result of which the portion 6a, due to this tensile stress snaps through the openings (unnumbered) of the fastener housing as a result of which the loop 7 in effect is no longer a loop and the constricting device 1 can be readily removed in the absence of the conventional telescopic removal heretofore described.

The fastener housing 2 is preferably constructed to plastic material which assists the tape 6 to slide therethrough. In addition, an underside of the clamping lever 3 (FIG. 4) is provided with a guide or slide strip 12 along its longitudinal axis between walls 3c, 3c thereof. This permits the portion 6a of the tape 6 to be drawn readily and easily through the openings of the housing 2 upon the depression of the lever 3 to its unclamped position.

While preferred forms and arrangements of parts have been shown in illustrating the invention, it is to be clearly understood that various changes in detail and arrangement of parts may be made without department from the spirit and scope of this disclosure.

I claim

1. A constricting device for increasing pressure in humans or animals comprisng an elongated member of flexible material having opposite ends, said elongated member being looped upon itself to dispose the ends thereof adjacent each other and dispose a loop remote therefrom, a fastener housing, said fastener housing having upper and lower sides, a passage through said fastener housing between said upper and lower sides, said elongated member being mounted for sliding movement in said passage with said opposite ends and loop being disposed at opposite ends of said fastener housing, said passage being of a transverse cross-section corresponding to the combined transverse cross-section of said ends, clamping means carried by said fastener housing for clamping against the end of said elongated member most closely adjacent said upper side of said fastener housing, means carried only by the end of said elongated member most closely adjacent said lower side of said fastener housing for abutting against said fastener housing to prevent said last-mentioned end from being drawn through said passage in a direction toward said loop, the end of said elongated member most closely adjacent said upper side of said fastener housing being devoid of means for abutting said fastener housing whereby only said last-mentioned end can pass completely through said passage in a direction toward said loop and said means carried by said end of said elongated member most closely adjacent said lower side of said fastener housing including a tongue having a terminal end directed downwardly and away from said lower side of said fastener housing.

2. The constricting device as defined in claim 1 wherein the end of said elongated member most closely adjacent said upper side of said fastener housing is received in a socket, and said socket is of a size and configuration to freely pass through said passage.

3. The constricting device as defined in claim 1 wherein said clamping means includes a clamping lever having a clamping end, a depressable end, and a medial portion therebetween, means pivotally mounting said clamping lever to said housing at its medial portion, and an elongated rib disposed beneath said depressable end with its longitudinal axis extending generally along the longitudinal axis of said elongated member for augmenting the free sliding of said elongated member through said housing upon the depression of said depressable end.

4. The constricting device as defined in claim 3 wherein said clamping end includes a rounded nose opposing the end of said elongated member most closely adjacent said upper side of said fastener housing.

* * * * *